US010981021B2

(12) United States Patent
Carpentier et al.

(10) Patent No.: US 10,981,021 B2
(45) Date of Patent: Apr. 20, 2021

(54) METHOD FOR TRANSIENTLY DISRUPTING A REGION OF THE BLOOD-BRAIN BARRIER OF A HUMAN

(71) Applicants: Carthera, Paris (FR); Assistance Publique Hopitaux de Paris, Paris (FR); Universite Pierre et Marie Curie (Paris 6), Paris (FR)

(72) Inventors: Alexandre Carpentier, Paris (FR); Michael Canney, Denver, CO (US); Alexandre Vignot, Lyons (FR)

(73) Assignees: Carthera, Paris (FR); Assistance Publique Hopitaux de Paris, Paris (FR); Universite Pierre et Marie Curie (Paris 6), Paris (FR)

( * ) Notice: Subject to any disclaimer, the term of this patent is extended or adjusted under 35 U.S.C. 154(b) by 882 days.

(21) Appl. No.: 15/067,334

(22) Filed: Mar. 11, 2016

(65) Prior Publication Data
US 2017/0259086 A1 Sep. 14, 2017

(51) Int. Cl.
*A61N 7/00* (2006.01)
*A61K 41/00* (2020.01)
*A61K 31/555* (2006.01)
*A61K 31/495* (2006.01)

(52) U.S. Cl.
CPC .............. *A61N 7/00* (2013.01); *A61K 31/495* (2013.01); *A61K 31/555* (2013.01); *A61K 41/0028* (2013.01); *A61N 2007/0021* (2013.01)

(58) Field of Classification Search
CPC ........ A61K 41/0028; A61N 2007/0021; A61N 2007/003
See application file for complete search history.

(56) References Cited

U.S. PATENT DOCUMENTS

| 10,322,178 | B2* | 6/2019 | Chen | A61K 9/5031 |
|---|---|---|---|---|
| 2008/0319355 | A1* | 12/2008 | Nita | A61N 7/00 601/2 |
| 2009/0005711 | A1* | 1/2009 | Konofagou | A61M 37/0092 601/2 |
| 2010/0143241 | A1* | 6/2010 | Johnson | A61K 41/0028 424/1.11 |
| 2012/0283502 | A1* | 11/2012 | Mishelevich | A61N 7/00 600/2 |
| 2016/0243234 | A1* | 8/2016 | Healey | A61K 9/0009 |
| 2019/0000493 | A1* | 1/2019 | Seip | A61B 8/0875 |

OTHER PUBLICATIONS

European Medicines Agency, "Assessment Report, SonoVue". May 2, 2014, EMA/454283/2014. (Year: 2014).*

(Continued)

*Primary Examiner* — Pascal M Bui Pho
*Assistant Examiner* — Yi-Shan Yang
(74) *Attorney, Agent, or Firm* — Cesari & McKenna, LLP

(57) ABSTRACT

The present invention relates to a method for transiently disrupting a region of the blood-brain barrier (BBB) of a human using ultrasounds in the presence of an ultrasound contrast agent, and uses thereof. The method comprises the application of at least one ultrasound (US) beam with a pressure level higher than 1 MPa and a resonance frequency ranging from 0.5 to 1.5 MHz.

33 Claims, 3 Drawing Sheets

(56) References Cited

OTHER PUBLICATIONS

Carpentier et al., "Clinical trial of blood-brain barrier disruption by pulsed ultrasound". Sci. Transl. Med. 2016, 8, 343. (Year: 2016).*
Idbaih et al., "Safety and feasibility of repeated and transient blood-brain barrier disruption by pulsed ultrasound in patients with recurrent glioblastoma". Clinical Cancer Research; 25(13) Jul. 1, 2019, pp. 3793-3801. (Year: 2019).*
Bader et al., "Sonothrombolysis". Adv. Exp. Med. Biol. 2016; 880:339-362. (Year: 2016).*
Ammi et al., "Characterization of ultrasound propagation through Ex-vivo human temporal bone". Ultrasound Med. Biol. Oct. 2008; 34(1): 1578-1589. (Year: 2008).*
Asquier et al "Blood-Brain Barrier Disruption in Humans Using an Implantable Ultrasound Device: Quantification with MR Images and Correlation with Local Acoustic Pressure" Journal of Neurosurgery, pp. 1-9, 2019.
Baseri et al "Multi-Modality Safety Assessment of Blood-Brain Barrier Opening Using Focused Ultrasound and Definity Microbubbles: A Short-Term Study" Ultrasound in Medicine and Biology vol. 36, pp. 1445-1459, 2010.
Chen et al "The Size of Blood-Brain Barrier Opening Induced by Focused Ultrasound is Dictated by the Acoustic Pressure" Journal of Cerebral Blood Flow and Metabolism vol. 34, pp. 1197-1204, 2014.
Choi et al "Microbubble-Size Dependence of Focused Ultrasound-Induced Blood-Brain Barrier Opening in Mice In Vivo" IEEE Transactions on Biomedical Engineering vol. 57, pp. 145-154, 2010.
Choi et al "Noninvasive and Localized Blood-Brain Barrier Disruption Using Focused Ultrasound can be Achieved at Short Pulse Lengths and Low Pulse Repetition Frequencies" Journal of Cerebral Blood Flow and Metabolism vol. 31, pp. 725-737, 2011.
Choi et al "Noninvasive and Transient Blood-Brain Barrier Opening in the Hippocampus of Alzheimer's Double Transgenic Mice Using Focused Ultrasound" Ultrasonic Imaging vol. 30, pp. 189-200, 2008.
Downs et al "Long-Term Safety of Repeated Blood-Brain Barrier Opening via Focused Ultrasound with Microbubbles in Non-Human Primates Performing a Cognitive Task" PLoS One vol. 10, pp. 1-26, 2015.
Idbaih et al "Safety and Feasibility of Repeated and Transient Blood-Brain Barrier Disruption by Pulsed Ultrasound in Patients with Recurrent Glioblastoma" pp. 1-24.
Kamimura et al "Chirp- and Random-Based Coded Ultrasonic Excitation for Localized Blood-Brain Barrier Opening" Physics in Medicine and Biology vol. 60, pp. 7695-7712, 2015.
Konofagou et al "Ultrasound-Induced Blood-Brain Barrier Opening" Current Pharmaceutical Biotechnology vol. 13, pp. 1332-1345, 2012.
Marquet et al "Feasibility Study of a Clinical Blood-Brain Barrier Opening Ultrasound System" Nano Life vol. 1, pp. 309-322, 2010.
McDannold et al "Temporary Disruption of the Blood-Brain Barrier by Use of Ultrasound and Microbubbles: Safety and Efficacy Evaluation in Rhesus Macaques" Cancer Research vol. 72, pp. 3652-3663, 2012.
O'Reilly et al "Blood-Brain Barrier: Real-Time Feedback-Controlled Focused Ultrasound Disruption by Using an Acoustic Emissions-Based Controller" Radiology vol. 263, pp. 96-106, 2012.
Tung et al "Feasibility of Noninvasive Cavitation-Guided Blood-Brain Barrier Opening Using Focused Ultrasound and Microbubbles in Nonhuman Primates" Applied Physics Letters vol. 98, pp. 1-3, 2011.
Vlachos et al "Permeability Assessment of the Focused Ultrasound-Induced Blood-Brain Barrier Opening Using Dynamic Contrast-Enhanced MRI" Physics in Medicine and Biology vol. 55, pp. 5451-5466, 2010.
Ammi et al "Characterization of Ultrasound Propagation Through Ex-Vivo Human Temporal Bone" Ultrasound in Medicine and Biology vol. 34, pp. 1578-1589, 2008.
Bader et al "Sonothrombolysis" Advances in Experimental Medicine and Biology vol. 880, pp. 339-362, 2016.
Saqqur et al "The Role of Sonolysis and Sonothrombolysis in Acute Ischemic Stroke: A Systematic Review and Meta-Analysis of Randomized Controlled Trials and Case-Control Studies" Journal of Neuroimaging vol. 24, pp. 209-220, 2014.

* cited by examiner

METHOD FOR TRANSIENTLY DISRUPTING A REGION OF THE BLOOD-BRAIN BARRIER OF A HUMAN

BACKGROUND

Field of the Invention

The invention generally relates to medical applications of ultrasound for opening the blood-brain barrier of a human. The invention more particularly relates to methods for opening the blood-brain barrier to substances that are not able to pass in efficient concentrations to tissue protected by the blood-brain barrier. The invention is particularly useful for the treatment of brain diseases in humans.

Background of the Invention

The blood-brain barrier (BBB) is formed of brain endothelial cells that separate the circulating blood from the central nervous system. The BBB is able to maintain a stable environment in the brain and protects the brain from chronic exposure to potentially damaging substances present in the blood stream, such as toxins, viruses, proteins or bacteria. However, the BBB may also prevent or delay the transport of substances that are potentially useful for treating brain diseases, such as chemotherapy drugs (except for some small molecule drugs with molecular weights of less than 0.4 kDa) or hydrophobic molecules. As a consequence, the BBB is also one of the largest obstacles to treating many brain diseases, including infections of the central nervous system, neurodegenerative diseases, brain cancers, etc., the diseased brain tissue being unable to receive from the systemic circulation a concentration of drugs sufficient to induce a therapeutic effect.

Thus, many techniques for delivering substances to the brain begin with the opening of the BBB before administering a substance into the blood stream. Previous attempts have been made to disrupt the BBB or to bypass it for enhancing drug delivery to the brain. For example, mannitol has been used as an osmotic substance, for increasing BBB permeability for particular drugs like methotrexate, carboplatin, etc. However, the injection of mannitol is often associated with side effects including hemorrhages, and the duration and magnitude of the BBB opening induced is difficult to control.

Convection enhanced delivery (CED) is another technique that has been explored to bypass the BBB. CED is performed by first inserting a small catheter directly into the targeted brain region and then by slowly infusing the drug directly into the tissue, thereby bypassing the BBB. Although CED has shown issues such as rapid drug elimination from tissue and limited drug penetration from the infusing catheter, the technique continues to be explored in clinical trials (White et al 2012), but has not gained widespread clinical acceptance.

Recently, a new technique has been proposed to temporarily disrupt the BBB and increase drug concentrations in the animal brain, using pulsed ultrasound (US). When US is applied to the brain in combination with systemic injection of an ultrasound contrast agent able to form micron-sized bubbles, the BBB permeability can be temporarily increased for a duration of six hours or more (Hynynen et al. 2001; McDannold et al. 2008; Park et al. 2012). More particularly, the US causes bubbles to form and grow in a target region where a substance is to be delivered through the BBB. The US energy is applied until the bubbles reach a condition that induces an opening in the BBB. This opening of the BBB has furthermore been shown to enhance the brain concentrations of systemically administered drugs (e.g. doxorubicin, BCNU, irinotecan, temozolomide, and trastuzumab) to therapeutic levels in pre-clinical studies (Treat et al. 2012; Liu et al. 2010; Wei et al. 2013; Beccaria et al. 2013; Park et al. 2012).

However, the application of US can also cause permanent biological damage in and around the BBB, including cell necrosis, a side effect that is unacceptable in human subjects.

Accordingly, there is a need in the art for a method for safely and temporarily disrupting the BBB in a human.

SUMMARY

By conducting clinical research, the inventors have discovered that ultrasound may be used to safely and temporarily disrupt the BBB of a human. Unexpectedly, the inventors have discovered that the application of US beams with a pressure level of greater than 1 MPa does not cause damage to human brain tissue. More particularly, the inventors have surprisingly discovered that US beams having a pressure level of greater than 1 MPa, in combination with the injection of an ultrasound contrast agent may be safely applied for disrupting the BBB for several hours. Whereas hemorrhagic lesions were observed in animals, from rabbits to primates, with US pressure levels of 0.5 or 0.8 MPa, US beams of 1.1 MPa or more are safely tolerated by human subjects and the degree of BBB disruption is sufficient to enhance the permeability of the BBB to therapeutic substances.

Therefore, the present invention relates to a method for transiently disrupting the blood-brain barrier (BBB) of a human using ultrasound in the presence of an ultrasound contrast agent, said method comprising the application to the brain of the patient of at least one ultrasound (US) beam with a pressure level higher than 1 MPa and a resonance frequency in a range between 0.5 and 1.5 MHz.

It is another object of the invention to provide a method of delivering a substance through the blood-brain barrier (BBB) of a human, comprising the injection of an ultrasound contrast agent and the application to the brain of the human of at least one ultrasound (US) beam with a pressure level higher than 1 MPa and a resonance frequency in a range between 0.5 and 1.5 MHz, and the administration of the substance.

A further object of the invention concerns a method for treating a brain disease, preferably a neurodegenerative disorder, in a human, said method comprising a step consisting of applying to the brain of the patient at least one ultrasound (US) beam with a pressure level higher than 1 MPa and a resonance frequency in a range between 0.5 and 1.5 MHz, in the presence of an ultrasound contrast agent.

The invention also relates to ultrasound contrast agents for use for transiently disrupting a region of the blood-brain barrier (BBB) of a human, wherein the ultrasound contrast agent is administered before or during the application, to the brain of the human, of at least one ultrasound (US) beam with a pressure level higher than 1 MPa and a resonance frequency in a range between 0.5 and 1.5 MHz.

Advantageously, solely a target region of the BBB is disrupted.

In some embodiments, the US beam is applied with a pressure level from 1.1 MPa to 2.0 MPa, preferably from 1.1 to 1.9 MPa, more preferably from 1.1 to 1.5 MPa. The inventors have surprisingly discovered that such US beam pressure levels allow to obtain an opening of the BBB, without inacceptable tissue damage.

Advantageously, the US beam has a mechanical index (MI) of approximately 1 to 2.0, preferably of 1.1 to 1.9, more preferably of 1.1 to 1.5.

In some embodiments, the US beam applied has a resonance frequency of 1.05 MHz and/or a pulse repetition rate of about 1 Hz.

In some embodiments, the US beams are applied with a pressure level comprised between 1.1 and 1.9 MPa, in pulses of duration about 25 ms and with a pulse repetition frequency of about 1 Hz.

In a particular embodiment, the US beam is a focused US beam. In another embodiment, the US beam is an unfocused US beam.

The methods of the invention may comprise a former step consisting of implanting a US transducer within a burr hole in the skull of the patient, the US beam being applied with the US transducer.

In some embodiments, the dose of ultrasound contrast agent administered to the patient is approximately 0.1 ml/kg with a maximum dose of up to 8.7 ml.

When a substance is administered, it is advantageously administered from 0 minutes to 10 hours after the application of the first US beams. In a particular embodiment, the substance is administered from 0 to 60 minutes after the application of the first US beams.

In some embodiments, the substance is administered together with the ultrasound contrast agent. The substance may be introduced into the blood stream, for instance by injection.

In some embodiments, the substance is a therapeutic or prophylactic agent, such as a chemotherapeutic drug.

Further features of the present invention will be apparent from the accompanying drawings and the following detailed description.

BRIEF DESCRIPTION OF THE DRAWINGS

The description below refers to the accompanying drawings, of which:

FIG. 4. MRI images from Patient 15. MR images of contrast-enhanced T1-weighted, FLAIR, and SWAN sequences for sonications 2 (top row) and 4 (bottom row) in Patient 15. The T1-weighted images are from 2 days prior to US sonications and 15 minutes after sonication. The FLAIR and SWAN sequences were obtained immediately after US disruption of the BBB by the implantable medical device. The rectangle shown is 20 mm×60 mm and highlights the region where BBB disruption was observed. Each of the axial images was aligned and centered on the acoustic axis of the US transducer. The implantable medical device had a slightly larger artifact on the SWAN sequence due to the higher susceptibility of this sequence, while there was negligible artifact on all other MR sequences. No tumor progression or adverse effects such as bleeding (SWAN) or additional inflammation (FLAIR) was observed in this patient after four sonications.

DETAILED DESCRIPTION

Figure 1:
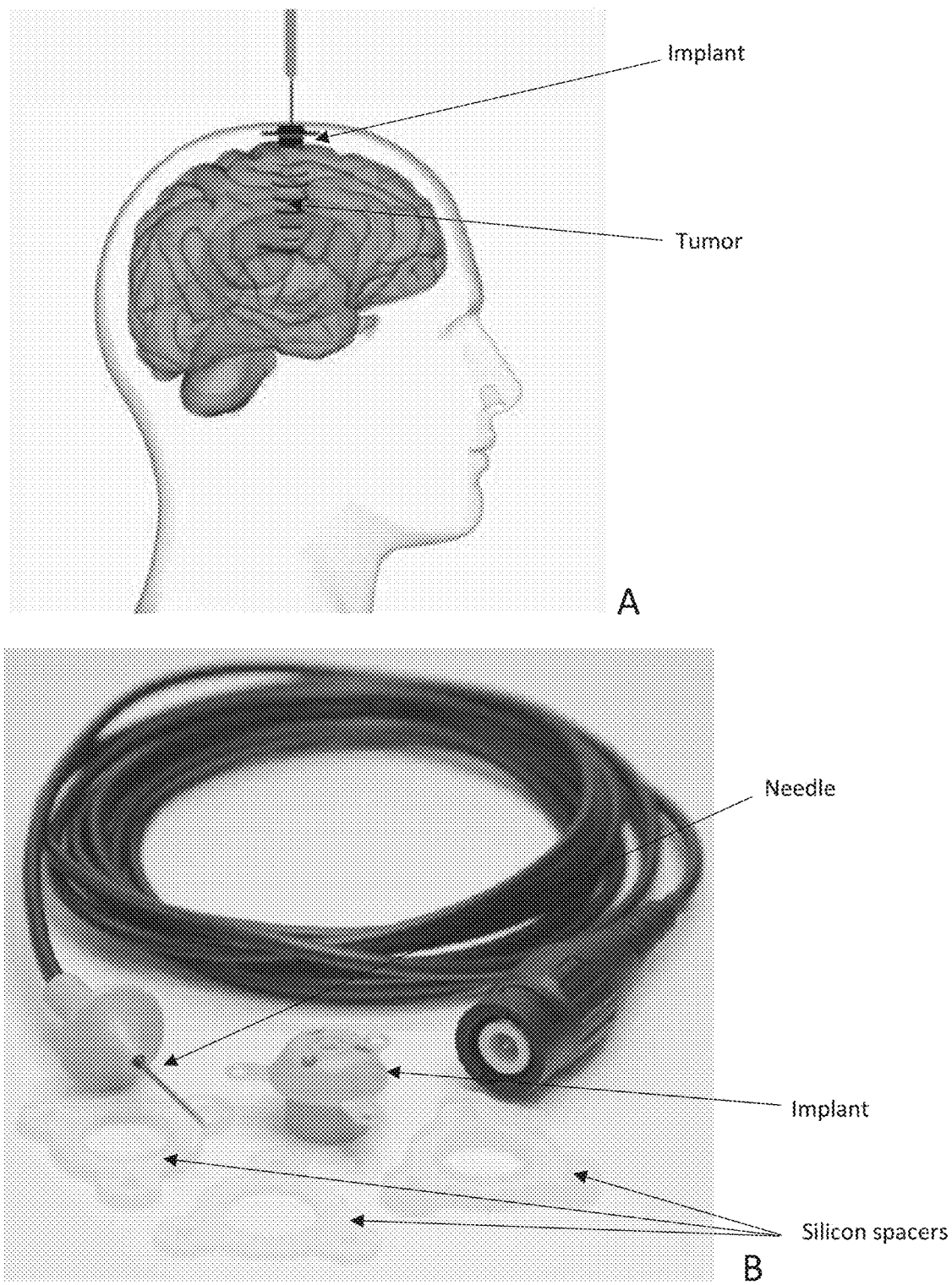
FIG. 1. The ultrasound implantable device. a) An implantable ultrasound (US) device is implanted in the skull bone thickness and connected to an external power supply via a transdermal needle connection during activation. b) The 11.5 mm diameter US implant consisted of a 10-mm diameter, 1 MHz ultrasound transducer encased in a biocompatible housing. The implant was passive and was connected via a transdermal needle to an external radiofrequency generator at each treatment to disrupt the BBB. Silicon spacers with thicknesses of 1, 2, and 3 mm were used between the implant and the skull bone to ensure that the front face of the transducer was flush with the inner surface of the skull bone.

Worldwide, the number of patients suffering from brain disease, including brain cancers and neurodegenerative disorders, is continuously increasing. The impermeability of the BBB has been identified as the main barrier for many therapies. In this context, safe and localized disruption of the BBB has been proven to present a significant challenge.

It is therefore an object of the present invention to provide a method for safely opening the BBB of a human using US. Uses thereof for delivering substances into the brain of the subject and/or for treating a brain disease are also described herein. The invention also relates to ultrasound contrast agent for use for transiently disrupting the BBB of a human, wherein the delivery of ultrasound contrast agent is combined with the application of ultrasound beam(s) to the brain of the human.

The present disclosure will best understood by reference to the following definitions.

Definitions

In the context of the invention, the term "disrupting the BBB", "opening the BBB" or "increasing the permeability of the BBB" are used interchangeably to refer to an increased susceptibility of the BBB to the passage of molecules therethrough that occurs without detectable damages of the brain tissue.

The term "ultrasound contrast agent" is used herein to refer to a substance (solid, liquid or gas) that is able to enhance the contrast between the region containing the agent and the surrounding tissue in an ultrasound image. Advantageously, the ultrasound contrast agent corresponds to small bubbles of a gas, termed "microbubbles," with an average diameter between 1 µm and 10 µm. Said microbubbles oscillate and vibrate when US is applied and may reflect ultrasound waves. The ultrasound contrast agent is generally injected intravenously into the blood stream, wherein it remains for a limited period of time.

The term "ultrasound beam", "ultrasound wave" and "ultrasound" are used indifferently for designating sound waves with frequencies higher than 20 kHz. The ultrasound energy may be focused ultrasound or unfocused ultrasound to treat a large zone of the BBB.

In the context of the invention, a "pulse" refers to a continuous burst, without interruption, of sinusoidal waves that may comprises several cycles.

The expression "sonication" is used to designate a complete ultrasound treatment that a subject can receive for a determined period of time, which may comprise several pulses.

As used herein, "subject" refers to a "human", i.e., a person of the species Homo sapiens, including man, woman, child and human at the prenatal stage. In one embodiment, a subject may be a "patient" who is awaiting the receipt of, or is receiving medical care or was/is/will be the object of a medical procedure, or is monitored for the diagnosis or the development of a disease.

In the context of the invention, the expression "brain" may designate all or part of the cerebral lobes (i.e., frontal lobe, parietal lobe and occipital lobe), including the cerebral cortex, but also the hypophysis and/or hypothalamus. As used herein, the expression "to the brain" means that the US beams are applied to at least a tissue of the central nervous system, whatever are the barriers to cross before (i.e., skull bone, dura mater, etc.).

In the context of the invention, the terms "treatment", "treat" or "treating" are used herein to characterize a therapeutic method or process that is aimed at (1) slowing down or stopping the progression, aggravation, or deterioration of the symptoms of the disease state or condition to which such term applies; (2) alleviating or bringing about ameliorations of the symptoms of the disease state or condition to which such term applies; and/or (3) reversing or curing the disease state or condition to which such term applies.

A "therapeutically effective amount" or "efficient concentration" refers to mean levels or amount of substance that is aimed at, without causing significant negative or adverse side effects to the target, delaying or preventing the onset of a disease, disorder, or condition related to a brain disease; slowing down or stopping the progression, aggravation, or deterioration of one or more symptoms of a brain disease; bringing about ameliorations of the symptoms of the disease, disorder, or condition related to a brain disease; reducing the severity or incidence of a brain disease; or curing a brain disease. A therapeutically effective amount may be administered prior to the onset of the brain disease, for a prophylactic or preventive action. Alternatively or additionally, the therapeutically effective amount may be administered after onset of the disease, for a therapeutic action.

Throughout the disclosure, various aspects of the invention can be presented in a range format. It should be understood that the description in range format is for convenience and brevity and should not be constructed as an inflexible limitation on the scope of the invention. Accordingly, the description of a range should be considered to have specifically disclosed all the possible subranges as well as individual numerical values within that range, range values being included.

Application of Ultrasound Beams

The present invention relates to the combined use of ultrasound contrast agent and ultrasound (US) beams, for transiently disrupting the BBB of a human.

According to the invention, the US beams are applied to the brain of the patient, with a pressure level higher than 1 MPa. In the context of the invention, the "pressure level" refers to the maximum acoustic pressure measured in the acoustic field of the device in water. Advantageously, the US beams are applied within a pressure range of 1.1 MPa to 3 MPa, preferably within a pressure range of 1.1 MPa to 2.5 MPa, more preferably within a pressure range of 1.1 MPa to 2.00, even more preferably within a pressure range of 1.1 MPa to 1.9, and most preferably within a pressure range of 1.1 MPa to 1.5 MPa. In a particular embodiment, the US beams are applied with a pressure level of 1.1 MPa. In another embodiment, the US beams are applied with a pressure level of 1.5 MPa. In a further embodiment, the US beams are applied with a pressure level of 1.9 MPa. Such pressure levels may be applied in a safe manner to human's brain, i.e., no detected damages of brain tissue are observed.

In the context of the invention, the value of the pressure level corresponds to the value onto the brain tissue. The pressure emitted by the device may be higher, to take into account potential attenuation of intervening tissues, such as skull bone attenuation. One skilled in the art will be able to adapt the value of the pressure level coming out of the emitter to obtain the required pressure level onto the brain.

According to the invention, the frequency of the US beam is between 0.5 and 1.5 MHz. More generally speaking, the frequency of the US beam does not exceed 2.0 MHz. In some embodiments, the frequency of the US beam is approximately 1.05 MHz. In some other embodiments, the frequency of the US beam is approximately 1.1 MHz.

The intensities of the US beams may be further characterized by mechanical index (MI) values that are less than 1.9 and preferably in the range of 1.05 to 1.8. In the context of the invention, the MI refers to the peak negative pressure in situ (MPa) divided by the square root of the frequency (MHz).

According to the invention, the US beams may be US focused beams or US unfocused beams. Preferably, the methods or uses of the invention are implemented with unfocused US beams.

According to the invention, the US may be applied using one or more transducers connected to an external generator.

In some embodiment, the US beams are applied by at least one transducer in contact with the skull bone, so that the US must pass through the skull bone and the dura mater to reach the brain tissue.

In some embodiments, the US beams are applied by at least one transducer in contact with the dura mater (behind the skull bone) of the subject. The ultrasound is thus emitted directly to the brain tissue, without having to pass the skull bone.

In some embodiments, the US beams are applied by at least one transducer in contact directly with the brain tissue, i.e., on an area wherein the dura mater has been removed.

In some embodiments, the transducer is an implantable medical device, which has been previously fixed to the skull of the patient. For instance, such implantable medical devices may be implanted in a burr hole of the skull of the patient following a surgical resection of a tumor, or during a dedicated surgical act. The implantable medical device may be maintained in the skull of the patient for days, weeks or months. It is then possible to perform repetitive BBB disruptions for a long period of time. The implant may be activated for each BBB disruption, for instance before each chemotherapy session of a patient in need thereof.

In some embodiments, the transducer is positioned to face a region of the brain that must receive the US beams. For instance, the target region may be a malignant or benign tumor region. In the context of the invention, "tumor region" refers to a region of the brain wherein abnormal cells grow. Accordingly, the expression "tumor region" may encompass tumor cells around or near a tumor and said tumor. In some embodiment, the transducer is placed regardless the position of the target region.

In some embodiments, several transducers, such as several implantable medical devices, are fixed to the skull of the patient, to cover different areas or a wider area of the brain. Advantageously, the transducers may be activated independently from each other. Alternatively, the transducers may be activated sequentially. Alternatively, all the transducers may be activated simultaneously.

In some embodiments, the US beams are applied by one or several external transducers, disposed on the head of the patient, through the skull bone and the dura mater.

In some embodiments, the method comprises the application of one or more pulses, or bursts, comprising from 100 to 100,000 successive cycles, preferably from 1,000 to 75,000, more preferably from 10,000 to 50,000, even more preferably from 20,000 to 30,000. In a particular embodiment, the method comprises the application of pulses of 25,000 successive cycles. In some embodiments, the mean burst duration of an ultrasound emission (i.e., the mean time from the start of a pulse to the end of that pulse) is between 10 msec. and 100 msec., preferably between 15 msec. and 50 msec., more preferably between 20 msec. and 30 msec., even more preferably approximately 25 msec.

The delay between two successive pulses is preferably from 30 msec. to 1000 msec. In a particular embodiment, the delay between two successive pulses is approximately 975 msec.

Advantageously, the successive pulses are applied within a total duration from 1 to 20 minutes. In a particular embodiment, the successive pulses are applied within a total duration that does not exceed 10 minutes, preferably 5 minutes. In a particular embodiment, the successive pulses are applied within a total duration of 150 seconds.

In a particular embodiment, pulses of 25,000 cycles are applied to the subject, at a pulse repetition frequency (PRF) of 1 Hz, every 1000 msec. with a pressure level of 1.1 MPa and a burst duration of about 23 msec. for a total duration of 150 seconds.

Ultrasound Contrast Agent

The method of the invention further requires the presence of an ultrasound contrast agent in the area of the BBB. The US contrast agent may be administered by injection, preferably by systemic injection. Examples of systemic injections include intravenous, subcutaneous, intramuscular, intradermal, intra vitreal and intraperitoneal injection, or perfusion.

In some embodiments, the ultrasound contrast agent is injected into the bloodstream of the subject.

Preferably, the ultrasound contrast agent is administered as a bolus just before the US beam application. More preferably, the US contrast agent is administered between 0 and 60 minutes before the US beam application. When successive US beams are applied, the ultrasound contrast agent is preferably delivered only once, just before the first US beam application of the cycle, though it may be delivered at activation of each US beam, or by a continuous infusion through the activation of successive US beams.

According to the invention, the ultrasound contrast agent may contain gaseous bubbles, a high concentration of gas, solid particles configured to vaporize in response to ultrasound, liquid configured to vaporize in response to ultrasound, micro particles configured to act as cavitation sites, solid particles having higher acoustic impedance than tissue in the desired region, and/or liquid with a high acoustic absorption coefficient.

In some embodiments, the ultrasound contrast agent is a microbubble contrast agent, preferably selected from the group consisting of sulphur hexafluoride microbubbles (SonoVue®), microbubbles made of an albumin shell and octafluoropropane gas core (Optison®), perflexane microbubbles encapsulated in an outer lipid shell (Imagent®), microbubbles made of octafluoropropane gas core encapsulated in an outer lipid shell (Definity®), or perfluorobutaine and nitrogen gas encapsulated in a lipid shell (BR38—Schneider et al., 2011). Preferably, the ultrasound contrast agent consists of sulphur hexafluoride microbubbles.

The microbubbles may have a mean diameter in a range from 1 µm to 10 µm. In some embodiments, the microbubbles have a mean diameter in a range from 4 µm to 5 µm. In some other embodiments, the microbubbles have a mean diameter in a range from 2 to 6 µm. In some embodiments, the microbubbles have a mean diameter of approximately 7 µm, 6 µm, 5 µm, 4 µm, 3 µm or 2 µm. In a particular embodiment, the microbubbles have a mean diameter of approximately 2.5 µm.

In some embodiments, the dose of ultrasound contrast agent ranges between 0.05 and 0.15 ml/kg based on the total weight of the subject. Preferably, the dose of ultrasound contrast agent is approximately 0.1 ml/kg. In a particular embodiment, the maximum dose of ultrasound contrast agent is up to 8.7 ml.

BBB Disruption

The application of US beams of more than 1 MPa to the brain tissue of a subject in the presence of an ultrasound contrast agent leads to the transient opening of the BBB. In the context of the invention, a "transient" opening refers to a reversible opening occurring preferably for more than 1 hour, the BBB returning after that to its initial state (i.e., the BBB state before the application of the first US beam).

In some embodiments, the BBB opening occurs for a period of time from 1 to 48 hours, preferably from 5 to 24 hours, more preferably from 6 to 10 hours. In some embodiments, the BBB opening occurs for approximately 8 hours.

In some embodiments, the BBB disruption is delimited, i.e., occurs solely in a target region of the BBB. For instance, only a region of the BBB surrounding damaged brain tissue, such as a tumor, is targeted. In other embodiments, the BBB disruption is generalized. To this end, focused US beams are preferably used, which may be easily focused onto a determined area of the brain to specifically and locally treat that area.

The disruption may be easily confirmed and/or evaluated by magnetic resonance imaging (MRI). For example, a gadolinium-based magnetic resonance (MR) contrast agent such as Dotarem® (gadoterate meglumine, Guerbet™ LLC USA), which does not normally cross the BBB, can be used to visualize the region of BBB disruption. When the agent is injected in a patient, a T1w MR sequence can be used to visualize regions of hypersignal and therefore visualize the effect of BBB disruption by ultrasound. BBB disruption typically leads to a change of 5-10% or more in MR signal enhancement after contrast agent administration. In addition, dynamic contrast enhanced (DCE) MR imaging techniques can be used to calculate the permeability of the BBB and to quantify the magnitude of the permeability enhancement after ultrasound sonications.

In some embodiments, an opening of the BBB refers to an opening of 0.1 to 10% of the BBB. In a particular embodiment, a volume of approximately 3 cm$^3$ is disrupted, corresponding to about 0.3% of the total volume of the brain. In another embodiment, a volume of 30 to 50 cm$^3$ is disrupted, corresponding to 3 to 5% of the total volume of the brain.

Treatment of Brain Diseases

It is another object of the invention to provide a method for treating a brain disease in a patient in need thereof, wherein the method comprises the transient disruption of the BBB of the patient by use of the combined application of US beams and ultrasound contrast agent described above.

Examples of brain diseases include neurodegenerative diseases and proliferative diseases.

Examples of neurodegenerative diseases include Parkinson's disease, Alzheimer's disease, Huntington's Disease (HD), schizophrenia, age associated memory impairment, and traumatic brain injury.

Examples of proliferative diseases include brain tumor, Gliomas, Meningiomas, Pituitary tumor, Pituitary adenomas, Nerve sheath tumors, Central neurocytoma, Choroid plexus carcinoma, Choroid plexus papilloma, Choroid plexus tumor, Dysembryoplastic neuroepithelial tumor, Ependymal tumor, Fibrillary astrocytoma, Giant-cell glioblastoma, Glioblastoma multiforme, Gliomatosis cerebri, Gliosarcoma, Hemangiopericytoma, Medulloblastoma, Medulloepithelioma, Meningeal carcinomatosis, Neuroblastoma, Neurocytoma, Oligoastrocytoma, Oligodendroglioma, Optic nerve sheath meningioma, Pediatric ependymoma, Pilocytic astrocytoma, Pinealoblastoma, Pineocytoma, Pleomorphic anaplastic neuroblastoma, Pleomorphic xanthoastrocytoma, Sphenoid wing meningioma, Subependymal giant cell astrocytoma, Subependymoma, Trilateral retinoblastoma, neurofibromatosis type I, neurofibromatosis type II, von Hippel-Lindau disease, tuberous sclerosis, Li-Fraumeni syndrome, Turcot syndrome type 1, Turcot syndrome type 2, and nevoid basal cell carcinoma syndrome.

In the context of the invention, the targeted brain diseases also encompass inflammatory and/or auto-immune diseases, such as multiple sclerosis or vascularitis. The brain diseases may also encompass innate or gained cerebral deficiencies, including intellectual deficiencies, mobility disability, cognitive impairments, sensorial deficiencies, etc. Diseases characterized by epileptic seizures, such as epilepsy, are also encompass.

The treatment of the brain disease may comprise the delivery of a substance to at least a target region of the brain tissue of the patient.

In some embodiments, the target region is a malignant tissue, for instance a malignant glioma.

In some embodiments, the method of treatment of the invention is applied following a partial or total surgical resection of a malignant tissue.

In some embodiments, the opening of the BBB may be used for improving the delivery of a substance, preferably in a therapeutic amount, to the brain of a patient, through the BBB. The substance may advantageously be a diagnostic agent, a prophylactic or therapeutic agent or any substance that may be required to target the brain of the patient.

Such agents may include chemotherapeutic agents, anti-inflammatory agents, immune-regulator agents, hormones, ion channel modifiers, neuroactive agents, genetic materials such as nucleic acids or cellular transplants that correct genetic deficiencies, accomplish genetic immunization, etc.

In some embodiments, the substance has a molecular size ranging from 50 to 200 kDa, preferably from 50 to 150 kDa.

The substance may be administered intravenously, intra arterially, sub-cutaneously, intra-muscularly, orally, sub-lingually or any delivery technique known in the art. Preferably, the substance is injected into the systemic circulation of the patient.

In some embodiments, the substance is delivered together with the ultrasound contrast agent.

In other embodiments, the substance is delivered separately, preferably after the ultrasound contrast agent. For instance, the substance is delivered within a period of time ranging from 10 minutes to 120 minutes after the BBB opening.

In some embodiments, the treatment of a brain disease consists solely to the application of US beams as described above (i.e., without the additional delivery of a therapeutic agent). Indeed, the progression of some brain diseases, such as for instance Alzheimer's, may be slowed down or stopped after application of US. For example, a loco regional sonodestruction or decomposition of pathological abnormal molecular deposit can be carried out by US applications according to the method of the invention.

In some embodiments, the application of US beams as described above (i.e., without the additional delivery of a therapeutic agent) may be used for treating cerebral deficiencies or epilepsies. Indeed, the application of such US beams may induce a beneficial neuro plasticity (i.e., dendritic sprouting and/or network reorganization) and/or increase the functionality of existing neurons and/or induce production of new-born neurons, etc.

In some embodiments, the method for treating a brain disease comprises the application of at least two sonications with a pressure level higher than 1 MPa and a resonance frequency ranging from 0.5 to 1.5 MHz, in the presence of an ultrasound contrast agent.

In some embodiment, the treatment may comprise between 2 and 6 separate sonications, and preferably at least 4 sonications.

Advantageously, a lag period separates two successive sonications, wherein no US beams are applied to the patient. The lag period preferably ranges from 1 to 45 days, more preferably from 15 to 30 days.

In some embodiments, the sonications are repeated every two, three, four, five, or more days.

In some embodiments, the sonications are repeated every two, three, four, five, or more weeks.

In some embodiments, the sonications are repeated every two, three, four, five, or more months.

In some embodiments, the sonications are repeated every week, twice a week, every two weeks, or once a month.

In some embodiments, the sonications are repeated every month, for a period of at least 2, 3, 4, 5 or more months.

According to the invention, the sonications may comprise US beams with different intensities, numbers of US beams, etc.

The present invention is further illustrated by the following example.

Example

Material and Methods
Patient Selection

Patients experiencing recurrence (first, second or third) of a histologically proven de novo glioblastoma (GBM), previously treated with at least the first line standard of care were included (i.e. radiation with concurrent and adjuvant temozolomide). Patients had to have a growing contrast-enhancing tumor of less than 35 mm in diameter and be eligible for carboplatin-based chemotherapy.

Methods

The trial was designed as a dose escalation study (Simon et al. 1997) in which the US pressure was increased throughout the study starting at 0.5 and increasing to 1.1 MPa through 5 different "dose" levels (0.50, 0.65, 0.80, 0.95, and 1.1 MPa). The initial US pressure was selected to be 0.5 MPa as this corresponded to the threshold for BBB opening found previously in small animal studies (Beccaria et al. 2013; McDannold et al. 2008).

A minimum of three patients were included at each dose level. If none of the patients experienced a dose-limiting toxicity (DLT), the next dose level was opened. If one patient experienced a DLT, three additional patients were enrolled at that dose level. If no additional patients had a DLT, then the dose level was increased after approval by the independent scientific monitoring committee.

Patients received US activation and BBB disruption every four weeks. The first treatment was performed at the initial "dose" level for the inclusion group, the second treatment at the next highest dose level, etc. Patients were treated monthly for up to a maximum of six treatments or until there was evidence of tumor progression.

Surgical Procedure

The ultrasound device was implanted within the skull bone in the tumor area (contrast enhancement region or high signal T2 FLAIR region). When the tumor was next to or within eloquent regions, the device was implanted in this critical area to attempt to prevent tumor progression and to have the highest potential enhancement to patient quality of life.

If patients were eligible for a new debulking surgery under general anesthesia, the device was implanted during this surgical procedure within a burr hole before skin closure. If surgical resection was unfeasible, the device was implanted during a dedicated surgical procedure in an ambulatory fashion and under local anesthesia. This procedure consisted of a 3-cm skin opening, creation of a burr hole, and finally implantation of the device and closure of the skin. In both cases, neuronavigation systems could be used to position the device in the desired location.

Monthly Magnetic Resonance Imaging Prior and After BBB Opening

All patients were assessed monthly using MR imaging, blood sampling, and clinical neurological evaluation. Two days prior to each planned ultrasound treatment, tumor status was evaluated on MRI according to the Response Assessment in Neuro-Oncology (RANO) Criteria (Wen et al. 2010). Progression-free survival (PFS) and overall survival (OS) were also assessed. Patients left the study if tumor progression was identified, which defined progression as an increase in tumor size of more than 25% or an increase in T2/FLAIR or as a neurological status degradation (Wen et al. 2010).

In the absence of tumor progression and significant toxicity, the BBB opening session followed by carboplatin injection was scheduled two days after. A subsequent MRI exam was taken immediately after US treatment (~10 minutes after US-induced BBB disruption). If tumor progression was observed, the patient exited the trial and received an alternative chemotherapy drug without BBB disruption.

Figure 4:
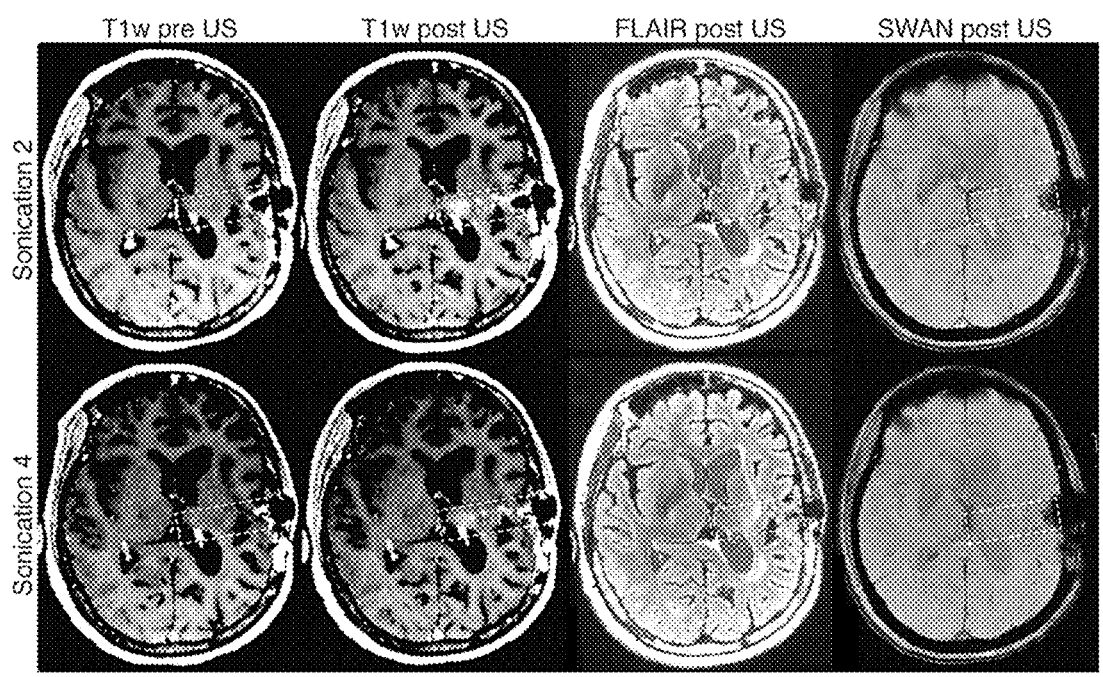
FIG. 4. MRI images from Patient 15. MR images of contrast-enhanced T1-weighted, fluid attenuated inversion recovery (FLAIR), and susceptibility weighted angiography sequences (SWAN) sequences for sonications 2 (top row) and 4 (bottom row) in Patient 15. The T1-weighted images are from 2 days prior to US sonications and 15 minutes after sonication. The FLAIR and SWAN sequences were obtained immediately after US disruption of the BBB by the implantable medical device. The rectangle shown is 20 mm×60 mm and highlights the region where BBB disruption was observed. Each of the axial images was aligned and centered on the acoustic axis of the US transducer. The implantable medical device had a slightly larger artifact on the SWAN sequence due to the higher susceptibility of this sequence, while there was negligible artifact on all other MR sequences. No tumor progression or adverse effects such as bleeding (SWAN) or additional inflammation (FLAIR) was observed in this patient after four sonications.

A 3T GE Signa MRI (GE Medical Systems™ Inc., Milwaukee, Wis.) was used for imaging exams. At each exam, standard FLAIR, T1w contrast enhanced (0.2 cc/kg, Dotarem®, Guerbet, France), SWAN, and diffusion sequences were obtained. T1w MR images were analyzed to grade the type of BBB opening observed. Four different grading criteria were used: Grade 0=no BBB opening, Grade 1=contrast enhancement in sub-arachnoid space, Grade 2=contrast enhancement in sub-arachnoid space and gray matter, and Grade 3=contrast enhancement in sub-arachnoid space, gray matter and white matter (FIG. 4).

Quantification of MR Contrast Enhancement After BBB Disruption

T1w gadolinium contrast enhancement was quantified by calculating the signal change in a 1-cm circular region of interest (ROI) in images obtained at the pre-sonication MRI (2 days before treatment) and in the images obtained immediately after US sonication using OsiriX™ software (Pixmeo SARL, Switzerland). The ROI was placed in the highest apparent T1 signal of the US region. The change in signal level in this ROI was corrected for changes in background signal by taking the average change in three separate ROIs outside of the tumor and sonication region. The pixel values were analyzed for significance before and after BBB disruption using a paired t-test analysis in statistical software (R Project, R Foundation for Statistical Computing, Vienna, Austria).

Ultrasound Sonication Parameters

The SonoCloud® US implant (CarThera®, Paris, France) consisted of a 10-mm diameter US transducer that had a resonance frequency of 1.05 MHz and that was encased in an 11.5 mm diameter biocompatible housing. The transducer was operated with a burst length of 25,000 cycles (23.8 ms) at a pulse repetition frequency of 1 Hz (2.38% duty cycle) for a total duration of 150 seconds. The implantable US transducer was passive and contained no internal power supply. To activate the device for 2.5 min, a transdermal needle connection device was connected to the implant and connected to an external radiofrequency generator. The external generator was custom-designed and contained a graphical user interface that guided the practitioner through the treatment protocol. The US pressure level was defined as the pressure at the near-field to far-field transition in water (12 mm distance from the source) and was calibrated using a procedure described in Beccaria et al. (2013). In the work reported here, the acoustic pressures noted are those in free-field water conditions at a distance of 12 mm from the front face of the transducer on the acoustic axis.

The US sonication was initiated at the beginning of a bolus injection of SonoVue® microbubbles (Bracco, Geneva, Switzerland). The initial clinical protocol was designed to have a dose of SonoVue corresponding to 0.1 cc/kg with a maximum dose of 4.8 cc (one vial of SonoVue®). After 18 treatments in nine patients that showed limited BBB opening, the French National Health Authority (ANSM) authorized an increase in SonoVue® to correspond to the weight of the patient at 0.1 cc/kg, thus subsequent patients received doses of SonoVue® that were dependent on their weight, with a maximum dose of up to 8.7 ml (87 kg patient) and a mean dose of 7.9 ml Carboplatin Chemotherapy Carboplatin dose (AUC, area under the curve) administration was calculated based on the Calvert formula taking into account renal function. Initial posology was AUC5, and further adapted (AUC4 or 6) based on biological analysis. Prior to Carboplatin injection, 80 mg of solumedrol was administered over 20 minutes. Intravenous Carboplatin perfusion started no later than 60 minutes after BBB opening and lasted for 60 to 90 minutes.

Results

Patient Enrollment and Treatment Characteristics

Characteristics of the first five groups of three patients that were treated in the trial are reported in Table 1.

TABLE 1

Patient history and treatment summary for the first three groups of patients included in the clinical trial.

| Group # | Patient # | Gender | Age | Recurrence # | Tumor size (mm) | Epilepsy & AED | Steroid daily dose | Tumor Resection* | # BBB opening sessions | Site of sonication |
|---|---|---|---|---|---|---|---|---|---|---|
| 1 | 1 | M | 38 | 2 | 30 | partial motor | 30 mg Hydro Cortisone | Yes | 3 | infiltrated brain & intratumoral |
| | 2 | M | 73 | 3 | 35 | partial motor | 0 | No | 2 | infiltrated brain |
| | 4 | F | 63 | 1 | 20 | partial motor | 40 mg Hydro Cortisone | Yes | 2 | infiltrated brain & intratumoral |
| 2 | 5 | M | 75 | 2 | 20 | generalized | 0 | No | 2 | infiltrated brain |
| | 6 | F | 77 | 1 | 35 | local | 10 mg Steroids | No | 4 | infiltrated brain & intratumoral |
| | 7 | F | 75 | 2 | 35 | 0 | 0 | Yes | 2 | intratumoral |
| 3 | 9 | M | 62 | 1 | 35 | 0 | 20 mg Steroids | Yes | 3 | infiltrated brain & intratumoral |
| | 10 | M | 69 | 2 | 25 | 0 | 0 | Yes | 4 | infiltrated brain |
| | 11 | M | 56 | 2 | 35 | local | 0 | No | 3 | infiltrated brain & intratumoral |
| 4 | 12 | F | 53 | 2 | 30 | partial sensitive | 0 | No | 2 | intratumoral |
| | 13 | M | 43 | 2 | 25 | generalized | 0 | Yes | 3 | infiltrated brain |
| | 14 | F | 59 | 1 | 30 | 0 | 30 mg Hydro Cortisone | No | 2 | intratumoral |
| 5 | 15 | F | 59 | 1 | 30 | partial sensitive | 0 | Yes | 4 | infiltrated brain & intratumoral |
| | 16 | M | 75 | 2 | 35 | generalized | 0 | Yes | 3 | infiltrated brain |
| | 17 | M | 59 | 2 | 30 | partial sensitive | 0 | Yes | 2 | infiltrated brain |

| Group # | Acoustic Pressure (MPa) | SonoVue ® Microbubble Dose (mL) | BBB opening grade | Mean T1 enhancement (%) | Carboplatin # cycles (AUC) | Duration on-study | Discontinuation cause | Tumor Progression (MRI, FLAIR/T1Gd) in the acoustic |
|---|---|---|---|---|---|---|---|---|
| 1 | 0.50 | 4.8 | 0 | n/a | 3 (5.5, 5) | 3 months | cystic progression | Yes |
| | 0.65 | 4.8 | 0 | | | | | |
| | 0.80 | 4.8 | 0 | | | | | |
| | 0.50 | 4.8 | 0 | n/a | 2 (5, 4) | 2 months | tumor progression | Yes |
| | 0.65 | 4.8 | 0 | | | | | |
| | 0.50 | 4.8 | 0 | n/a | 2 (5, 5) | 2.5 months | tumor progression | Yes |
| | 0.65 | 4.8 | 0 | | | | | |
| 2 | 0.65 | 4.8 | 0 | n/a | 2 (5, 4) | 2 months | tumor progression | Yes |
| | 0.80 | 4.8 | 0 | | | | | |
| | 0.65 | 4.8 | 0 | n/a | 3 (5.5, 5) | >5 months | 4 mm diam distant stroke | No |
| | 0.50 | 4.8 | 1 | 20 | | | | |
| | 0.80 | 4.8 | 1 | 13 | | | | |
| | 0.95 | 4.8 | 0 | n/a | | | | |
| | 0.65 | 4.8 | 0 | n/a | 2 (5, 5) | 2 months | tumor progression | Yes |
| | 0.80 | 4.8 | 1 | 10 | | | | |
| 3 | 0.80 | 4.8 | 0 | n/a | 3 (5.5, 5) | >4 months | pulmonary embolism | No |
| | 0.80 | 8.7 | 1 | 8 | | | | |
| | 0.95 | 8.7 | 2 | 16 | | | | |
| | 0.80 | 4.8 | 1 | 11 | 4 (5.5, 5.5) | 4 months | tumor progression | No |
| | 0.80 | 7.3 | 2 | 8 | | | | |
| | 0.95 | 7.3 | 2 | 11 | | | | |
| | 1.10 | 7.3 | 3 | 9 | | | | |
| | 0.80 | 4.8 | 1 | 16 | 3 (5.5, 5) | 3 months | tumor progression | No |
| | 0.80 | 8.1 | 1 | 5 | | | | |
| | 0.95 | 8.1 | 2 | 11 | | | | |
| 4 | 0.95 | 5.0 | 1 | 20 | 2 (5, 5) | 2 months | tumor progression | No |
| | 1.10 | 5.0 | 2 | 10 | | | | |
| | 0.95 | 7.3 | 1 | 15 | 3 (5.5, 5) | 3 months | tumor progression | No |
| | 1.10 | 7.5 | 1 | 30 | | | | |
| | 1.10 | 7.9 | 2 | 29 | | | | |
| | 0.95 | 7.0 | 1 | 11 | 2 (5, 5) | 2 months | tumor progression | No |
| | 1.10 | 7.0 | 2 | 16 | | | | |
| 5 | 1.10 | 6.0 | 3 | 5 | 4 (5.5, 5.4) | still on study | no progression | No |
| | 1.10 | 6.0 | 3 | 23 | | | | |
| | 1.10 | 6.3 | 3 | 11 | | | | |
| | 1.10 | 6.3 | 3 | | | | | |

TABLE 1-continued

Patient history and treatment summary for the first three groups of patients included in the clinical trial.

| | | | | | | | |
|---|---|---|---|---|---|---|---|
| 1.10 | 7.4 | 2 | 7  | 3 (5.5, 5) | 3 months | tumor progression | No |
| 1.10 | 7.4 | 2 | 18 |            |          |                   |    |
| 1.10 | 7.4 | 2 | 19 |            |          |                   |    |
| 1.10 | 8.0 | 1 | 8  | 2 (5, 5)   | 2 months | tumor progression | slight |
| 1.10 | 8.0 | 3 | 37 |            |          |                   |        |

Patient 3 (excluded from table) did not receive ultrasound treatment due to a later diagnosis of radionecrosis. Patient 8 (excluded from table) had spontaneous micro hemorrhages on pre-sonication MRI and sonications were cancelled. *, device implantation with or without surgical resection. The sonication site was either in the infiltrative brain area, which was a hypersignal on FLAIR MR images or in the intratumor region or was in both regions. BBB opening grade is defined as Grade 0 = no BBB opening, Grade 1 = contrast enhancement in sub-arachnoid space, Grade 2 = contrast enhancement in sub-arachnoid space and gray matter, Grade 3 = contrast enhancement in sub-arachnoid space, gray matter and white matter.

Two additional patients were enrolled but not treated: (i) patient 3 was found to have radionecrosis after one-time surgery including surgical resection and device implantation, and (ii) patient 8 was found to have spontaneous micro hemorrhages on pre-sonication MRI and thus did not receive any US.

The sex ratio, male/female, was 2:1. The median age at inclusion was 68 years old. All patients included had GBM recurrence: (i) first recurrence in 3 patients, (ii) second recurrence in 5 patients, and (iii) third recurrence in 1 patient. Six were being treated for epileptic seizures with levetiracetam and four out of nine were being treated using steroids. All patients had tumors with a maximum diameter on contrast-enhanced MRI of less than 35 mm at inclusion.

While the trial was planned to deliver a maximum of 6 treatments over the course of 6 months, the first 9 patients received between 2-4 US-carboplatin treatments (mean=2.8, median=3) before they exited the trial for tumor progression.

Efficacy of BBB Opening

Figure 2:
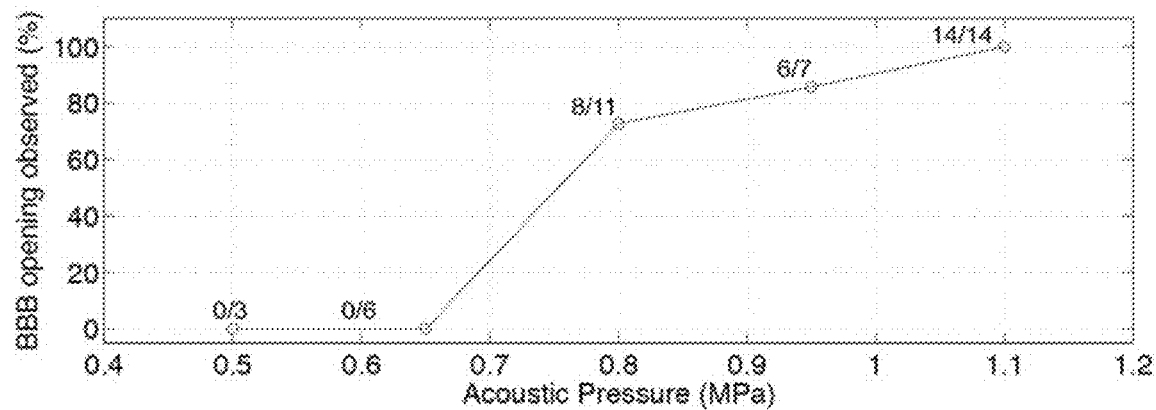
FIG. 2. Summary of BBB opening observed versus acoustic pressure. The initial group of patients was first treated at an acoustic pressure of 0.5 MPa with the 1 MHz ultrasound implant. The subsequent groups were initially treated at 0.65 MPa and 0.8 MPa and progressed up to 1.1 MPa.

Twenty-five sonications in total were performed in these five groups of patients. A summary of the BBB opening observed is shown in FIG. 2, while the relative "grade" of opening is shown in Table 1. The first group of patients was first treated at an acoustic pressure of 0.5 MPa, while the second group started at an acoustic pressure of 0.65 MPa. In these treatments at 0.5 and 0.65 MPa, no BBB disruption was observed on contrast-enhanced T1-weighted MRI. BBB disruption was observed in 8/11 sonications at 0.8 MPa, in 3/4 sonications at 0.95 MPa, and in 1/1 sonication at 1.1 MPa.

Figure 3:
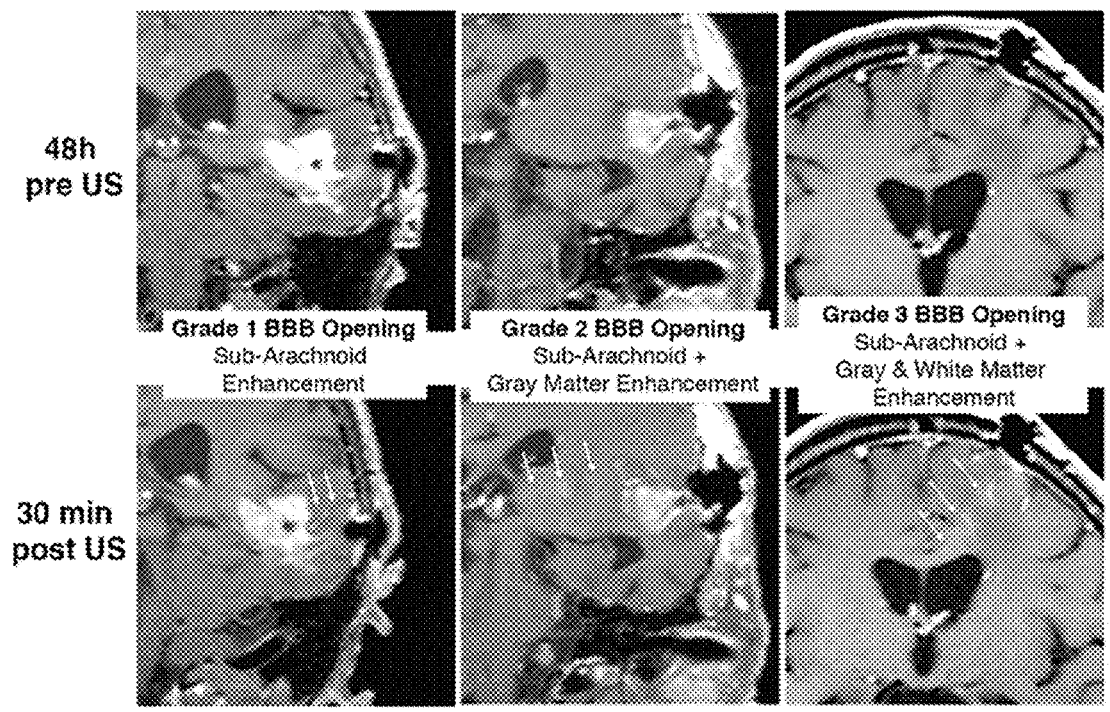
FIG. 3. The images show the T1 contrast-enhanced images obtained two days prior to US and immediately, e.g., 30 min., after ultrasound treatments. The regions of enhancement due to US sonications are indicated by the white arrows in each post sonication image. The different grades of BBB disruption observed on contrast-enhanced T1w MRI: Grade 1=contrast enhancement in sub-arachnoid space (MRI of Patient 6, Session 3 at 0.8 MPa), Grade 2=contrast enhancement in sub-arachnoid space and gray matter (MRI of Patient 9, Session 3 at 0.95 MPa), Grade 3=contrast enhancement in sub-arachnoid space, gray and white matter (MRI of Patient 10, Session 4 at 1.1 MPa).

The different grades of BBB disruption observed on contrast-enhanced T1w MRI are shown in FIG. 3. These images show the T1 contrast-enhanced images obtained two days prior to US and immediately, e.g., 30 min., after ultrasound treatments in Patient 6 (Session 3), Patient 9 (Session 3), and Patient 10 (Session 4).

In addition to analysis and grading of the enhancement observed on T1w images, the mean T1 enhancement was quantified using a 1-cm diameter ROI in the region of maximum enhancement and is shown in Table 1. The mean enhancement across all treatments where BBB opening was observed was 11% (range=5%-20%) and all levels of enhancement of ROIs when compared using paired t-tests were highly significant (p values all<0.002).

The median progression free survival (PFS) observed in the trial for the first nine patients was three months. Tumor progression occurred distant to the US field, only when BBB was opened using at least 0.8 MPa acoustic pressure. Patients treated at the highest US dose levels did not have tumor progression on T1 or FLAIR images within the US field.

Safety and Toxicity

The US disruption of the BBB was well tolerated in all patients. No evidence of acute hemorrhage/ischemia/oedema was observed in post-sonication Swann T2, Diffusion or FLAIR sequences. Three adverse events occurred: (1) venous inflammation in a patient's arm due to chemotherapy extravasation, (2) one pulmonary embolism, and (3) an asymptomatic 5 mm cerebellum stroke. None of these events where considered to be related to ultrasound treatments by the independent scientific monitoring committee. Patients did not present any clinical symptoms or sensation during the 2.5 min US emission, although BBB opening was generally performed in eloquent areas. When sonications were performed in the language/motor areas, patients maintained speaking/movement during the BBB opening/US activation to verify the absence of US-induced neuronal sideration. Patients did not present any clinical symptoms in the hours or days following BBB disruption, confirming the absence of US-induced neuronal sideration. The epileptic status of patients was unchanged before and after BBB opening sessions. No cerebral carboplatin-related toxicity was observed. When patient conditions deteriorated, it was due to tumor progression, with tumor-related clinical symptoms in agreement with radiological tumor progression.

REFERENCES

Hynynen, K., McDannold, N., Vykhodtseva, N., and Jolesz, F. (2001). Noninvasive MR Imaging—guided Focal Opening of the Blood-Brain Barrier in Rabbits. Radiology, 220(3):640-646.

McDannold, N., Vykhodtseva, N., and Hynynen, K. (2008). Blood-brain barrier disruption induced by focused ultrasound and circulating preformed microbubbles appears to be characterized by the mechanical index. Ultrasound Med. Biol., 34(5):834-840.

Park, J., Zhang, Y., Vykhodtseva, N., Jolesz, F. A., and McDannold, N. J. (2012). The kinetics of blood brain barrier permeability and targeted doxorubicin delivery into brain induced by focused ultrasound. Journal of Controlled Release, 162(1):134-142.

Treat, L., McDannold, N., Zhang, Y., Vykhodtseva, N., and Hynynen, K. (2012). Improved anti-tumor effect of liposomal doxorubicin after targeted blood-brain barrier disruption by MRI-guided focused ultrasound in rat glioma. Ultrasound Med. Biol., 38(10):1716-1725.

Liu, H.-L., Hua, M.-Y., Chen, P.-Y., Chu, P.-C., Pan, C.-H., Yang, H.-W., Huang, C.-Y., Wang, J.-J., Yen, T.-C., and Wei, K.-C. (2010). Blood-brain barrier disruption with focused ultrasound enhances delivery of chemotherapeutic drugs for glioblastoma treatment. Radiology, 255(2): 415-425.

Wei, K.-C., Chu, P.-C., Wang, H.-Y. J., Huang, C.-Y., Chen, P.-Y., Tsai, H.-C., Lu, Y.-J., Lee, P.-Y., Tseng, I.-C., Feng, L.-Y., Hsu, P.-W., Yen, T.-C., and Liu, H.-L. (2013). Focused ultrasound-induced blood-brain barrier opening to enhance temozolomide delivery for glioblastoma treatment: a preclinical study. PLoS One, 8(3):e58995.

Beccaria, K., Canney, M., Goldwirt, L., Fernandez, C., Adam, C., Piquet, J., Autret, G., Clement, O., Lafon, C., Chapelon, J., and Carpentier, A. (2013). Opening of the blood-brain barrier with an unfocused ultrasound device in rabbits. J. Neurosurg., 119(4):887-898.

Wen, P. Y., Macdonald, D. R., Reardon, D. A., Cloughesy, T. F., Sorensen, A. G., Galanis, E., Degroot, J., Wick, W., Gilbert, M. R., Lassman, A. B., Tsien, C., Mikkelsen, T., Wong, E. T., Chamberlain, M. C., Stupp, R., Lamborn, K. R., Vogelbaum, M. A., van den Bent, M. J., and Chang, S. M. (2010). Updated response assessment criteria for high-grade gliomas: response assessment in neuro-oncology working group. J Clin Oncol, 28(11):1963-72.

White, E., Bienemann, A., Taylor, H., Hopkins, K., Cameron, A., and Gill, S. (2012). A phase i trial of carboplatin administered by convection-enhanced delivery to patients with recurrent/progressive glioblastoma multiform. Contemp Clin Trials, 33(2):320-31.

Park, J., Zhang, Y., Vykhodtseva, N., Jolesz, F. A., and McDannold, N. J. (2012). The kinetics of blood brain barrier permeability and targeted doxorubicin delivery into brain induced by focused ultrasound. Journal of Controlled Release, 162(1):134-142.

Schneider, M., Anantharam, B., Arditi, M., Bokor, D., Broillet, A., Bussat, P., Fouillet, X., Frinking, P., Tardy, I., Terrettaz, J., et al. (2011). Br38, a new ultrasound blood pool agent. Investigative radiology, 46(8):486-494.

The invention claimed is:

1. An in vivo method for transiently disrupting a region of a blood-brain barrier (BBB) of a human using ultrasound and an ultrasound contrast agent, said method comprising administering a dose of the ultrasound contrast agent to the human and applying onto the brain of the human at least one ultrasound (US) beam with a pressure level in a range of 1 to 1.1 MPa and a resonance frequency ranging from 0.5 to 1.5 MHz, with a mean pulse of duration between 10 msec and 50 msec.

2. The in vivo method of claim 1, wherein the pressure level of the at least one US beam is 1.1 MPa.

3. The in vivo method of claim 1, wherein the at least one US beam has a mechanical index (MI) ranging from 1 to 2.00.

4. The in vivo method of claim 1, wherein the at least one US beam is applied in pulses of duration between 20 ms and 30 ms and a pulse repetition frequency of 1 Hz.

5. The in vivo method of claim 1, wherein the at least one US beam is focused or unfocused.

6. The in vivo method of claim 1, wherein the dose of the ultrasound contrast agent administered to the human is 0.1 ml/kg with a maximum volume of 8.7 ml.

7. The in vivo method of claim 1, wherein the pressure level of the at least one US beam is 1.1 MPa and the at least one US beam is applied in pulses of duration between 20 ms and 30 ms and with a pulse repetition frequency of 1 Hz.

8. The in vivo method of claim 1, further comprising, before the applying step, a step consisting of implanting a US transducer within a burr hole in the skull of the human, wherein the at least one US beam is applied with the US transducer.

9. The in vivo method of claim 7, further comprising, before the applying step, a step consisting of implanting a US transducer within a burr hole in the skull of the human, wherein the at least one US beam is applied with the US transducer.

10. An in vivo method of delivering a substance through a blood-brain barrier (BBB) of a human, comprising injecting the human with a dose of an ultrasound contrast agent, applying to the brain of the human at least one ultrasound (US) beam with a pressure level in a range of 1 to 1.1 MPa and a resonance frequency ranging from 0.5 to 1.5 MHz, with a mean pulse of duration between 10 msec and 50 msec, thereby disrupting the BBB, and administering the substance to the human.

11. The in vivo method of claim 10, wherein the pressure level of the at least one US beam is 1.1 MPa.

12. The in vivo method of claim 10, wherein the at least one US beam has a mechanical index (MI) ranging from 1 to 2.00.

13. The in vivo method of claim 10, wherein the resonance frequency of the at least one US beam is 1.05 MHz and/or the at least one US beam has a pulse repetition frequency of 1 Hz.

14. The in vivo method of claim 10, wherein the at least one US beam is focused or unfocused.

15. The in vivo method of claim 10, wherein the dose of the ultrasound contrast agent injected into the human is 0.1 ml/kg with a maximum volume of 8.7 ml.

16. The in vivo method of claim 10, wherein the at least one US beam is applied in pulses of duration between 20 ms and 30 ms and with a pulse repetition frequency of 1 Hz.

17. The in vivo method of claim 16, further comprising, before the applying step, a step consisting of implanting a US transducer within a burr hole in the skull of the human, wherein the at least one US beam is applied with the US transducer.

18. The in vivo method of claim 10, further comprising, before the applying step, a step consisting of implanting a US transducer within a burr hole in the skull of the human, wherein the at least one US beam is applied with the US transducer.

19. The in vivo method of claim 10, wherein the substance is administered from 0 to 60 minutes after the disruption of the BBB.

20. The in vivo method of claim 10, wherein the substance is a therapeutic or prophylactic agent.

21. The in vivo method of claim 10, wherein the substance is a chemotherapeutic drug.

22. An in vivo method for treating a brain disease in a human in which an ultrasound contrast agent is present, said method comprising a step consisting of applying to the brain of the human at least one ultrasound (US) beam with a pressure level in a range of 1 to 1.1 MPa and a resonance frequency ranging from 0.5 to 1.5 MHz, with a mean pulse of duration between 10 msec and 50 msec, thereby disrupting a blood brain barrier (BBB) in the human.

23. The in vivo method of claim 22, wherein the pressure level of the at least one US beam is 1.1 MPa.

24. The in vivo method of claim 22, wherein the at least one US beam has a mechanical index (MI) ranging from 1 to 2.00.

25. The in vivo method of claim 22, wherein the resonance frequency is 1.05 MHz and/or the pulse repetition frequency is 1 Hz.

26. The in vivo method of claim 22, wherein the at least one US beam is focused or unfocused.

27. The in vivo method of claim 22, wherein a dose of the ultrasound contrast agent present in the human is 0.1 ml/kg with a maximum volume of 8.7 ml.

28. The in vivo method of claim 22, wherein the at least one US beam is applied in pulses of duration between 20 ms and 30 ms and with a pulse repetition frequency of 1 Hz.

29. The in vivo method of claim 28, further comprising, before the applying step, a step consisting of implanting a US transducer within a burr hole in the skull of the human, wherein the at least one US beam is applied with the US transducer.

30. The in vivo method of claim 22, further comprising, before the applying step, a step consisting of implanting a US transducer within a burr hole in the skull of the human, wherein the at least one US beam is applied with the US transducer.

31. The in vivo method of claim 22, further comprising administering a substance from 0 to 60 minutes after the disruption of the BBB.

32. The in vivo method of claim 31, wherein the substance is a therapeutic or prophylactic agent.

33. The in vivo method of claim 31, wherein the substance is a chemotherapeutic drug.

\* \* \* \* \*